United States Patent
Laske et al.

(10) Patent No.: US 7,177,704 B2
(45) Date of Patent: Feb. 13, 2007

(54) PACING METHOD AND APPARATUS

(75) Inventors: Timothy G. Laske, Shoreview, MN (US); Terrell M. Williams, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 400 days.

(21) Appl. No.: 10/135,909

(22) Filed: Apr. 29, 2002

(65) Prior Publication Data

US 2003/0204233 A1    Oct. 30, 2003

(51) Int. Cl.
*A61N 1/00* (2006.01)
(52) U.S. Cl. .................. 607/126; 607/127; 600/375
(58) Field of Classification Search ........ 607/126–132; 600/375
See application file for complete search history.

(56) References Cited

U.S. PATENT DOCUMENTS

| | | | |
|---|---|---|---|
| 4,010,758 A | 3/1977 | Rockland et al. | |
| 4,149,542 A | 4/1979 | Thorén | 128/418 |
| 4,506,680 A | 3/1985 | Stokes | 128/786 |
| 4,577,642 A | 3/1986 | Stokes | 128/784 |
| 4,603,704 A | 8/1986 | Mund et al. | 128/784 |
| 4,606,118 A | 8/1986 | Cannon et al. | 29/825 |
| 4,677,989 A | 7/1987 | Robblee | 128/784 |
| 4,711,251 A | 12/1987 | Stokes | 128/784 |
| 4,773,433 A | 9/1988 | Richter et al. | 128/784 |
| 4,784,160 A | 11/1988 | Szilagyi | 128/784 |
| 4,784,161 A | 11/1988 | Skalsky et al. | 128/785 |
| 4,819,661 A | 4/1989 | Heil, Jr. et al. | 128/786 |
| 4,819,662 A | 4/1989 | Heil, Jr. et al. | 128/786 |
| 4,886,074 A | 12/1989 | Bisping | |
| 5,231,996 A | 8/1993 | Bardy et al. | |
| 5,246,014 A | 9/1993 | Williams et al. | |
| 5,320,642 A | 6/1994 | Scherlag | |
| 5,487,758 A | 1/1996 | Hoegnelid et al. | |
| 5,545,201 A | 8/1996 | Helland et al. | |
| 5,728,140 A | 3/1998 | Salo et al. | |
| 5,759,202 A * | 6/1998 | Schroeppel | 607/126 |

(Continued)

FOREIGN PATENT DOCUMENTS

WO    WO 02/22206 A1    3/2002

OTHER PUBLICATIONS

Absract Deshmukh, P. et al., "Permanent Direct His Bundle Pacing: Long Term Experience," *Bradycardia IV: Pacemaker Implantation Techniques*, Version 30, Ch. 176 (May 5, 2001).

(Continued)

*Primary Examiner*—Mark Bockelman
(74) *Attorney, Agent, or Firm*—Carol F. Barry; Girma Wolde-Michael

(57) ABSTRACT

The present invention provides for a method and apparatus providing pacing to improve the hemodynamics of the heart for patients with AV nodal block, right/left bundle branch block, and heart failure. A lead body having at least one conductor with an insulative sleeve is introduced into the right atrium of a heart. A partially masked helical electrode connected to the conductor is then secured preferably into the atrial aspect of the atrioventricular septum. The electrical conductor is then rotated such that an unmasked portion of the electrode is moved to a depth within the heart tissue substantially near the heart's intrinsic conduction system. This method and apparatus allow pacing in a natural manner via low power stimulation of the heart's intrinsic conduction system.

22 Claims, 9 Drawing Sheets

U.S. PATENT DOCUMENTS

| | | | |
|---|---|---|---|
| 5,851,226 | A | 12/1998 | Skubitz et al. |
| 5,871,531 | A * | 2/1999 | Struble .................... 607/126 |
| 6,038,463 | A | 3/2000 | Laske et al. |
| 6,078,840 | A | 6/2000 | Stokes |
| 6,178,355 | B1 | 1/2001 | Williams et al. |
| 6,298,272 | B1 | 10/2001 | Peterfeso et al. |
| 6,304,786 | B1 * | 10/2001 | Heil et al. ............. 607/126 |

OTHER PUBLICATIONS

Nielsen, JC, "Optimal Pacing Mode in Patients with Sick Sinus Syndrome,", *Faculty of Health Sciences, PhD*, p. 261-2 (2000).

Saxon, L. et al., "Increased Risk of Progressive Hemodynamic Deterioration in Advanced Heart Failure Patients Requiring Permanent Pacemakers," *American Heart Journal*, vol. 125, No. 8, pt. 1, p. 1306-10 (May 1993).

Abstract, Yasuteru, Y. et al., "Significant Reduction of Mitral Regurgitation by Direct His-Bundle Pacing or Right Venticular Outflow Septal Pacing in Comparison with Right Ventricular Apical Pacing in Patients with Chronic Atrial Fibrillation and Mitral Regurgitation," *Bradycardia IV: Pacemaker Implantation Techniques*, Ch. 178 (May 5, 2001).

* cited by examiner

PACING METHOD AND APPARATUS

FIELD OF THE INVENTION

The present invention generally relates to the field of implantable medical devices, and more particularly to a medical electrical lead providing improved pacing capabilities.

BACKGROUND OF THE INVENTION

Various types of pacing leads have been developed for endocardial introduction into different chambers of a patient's heart, typically the right ventricle or right atrial appendage, as well as the coronary sinus. These flexible leads usually are constructed having an outer polymeric sheath encasing one or more electrical conductors. One conductor is typically attached at its distal end to the shank portion of a tip electrode. In bipolar or multipolar leads, one or more further conductors are provided in coaxial or co-linear relation to the first conductor and are connected at their distal end to a more proximally located, ring-shaped electrode situated along the lead body. The proximal ends of each conductor are each coupled to a connector, which includes a single pin in unipolar leads, and additional pins or in-line rings in bipolar and multipolar leads.

These pacing leads can be attached to a variety of pacing devices such as a single chamber atrial pacemaker (AAI), a single chamber ventricular pacemaker (VVI), or a dual chamber pacemaker (DDD). In a conventional AAI or VVI pacemaker, only one lead is required. Stimulation in the AAI pacemakers is normally performed with the lead located in the right atrium. Stimulation with a VVI pacemaker normally takes place in the apex of the right ventricle. The conventional DDD pacemaker requires two leads. Similar to AAI pacing, one of the DDD pacemaker leads is placed in the heart's right atrium and similar to VVI pacing another DDD pacemaker lead is placed in the apex of the right ventricle. The leads are used to sense electrical activity in the heart and to deliver stimulation pulses when spontaneous electrical activity ceases. The leads are often shaped so the atrial lead and the ventricular lead are adapted to conform to their desired placement in the heart when the electrode system is implanted. In a DDD lead system, the implantation of dual curved leads has proven difficult due to the complicated nature of implanting two curved leads into two separate chambers of the heart.

In a healthy heart an electrical impulse starts at the sinoatrial (SA) node located in the upper right of the right atrium and travels to the right and left atria through the myocyte cells, depolarizing the cells and causing them to contract together. This action generally takes about 0.04 seconds. The electrical impulse then travels to the atrioventricular node (AV node) located in the lower left side of the right atrium. A natural delay occurs which allows the atria to contract and the ventricles to fill up with blood. Next, the electrical impulse travels to the bundle of His located in the interventricular septum and divides into the right and left bundle branches where it rapidly spreads through the purkinje fibers to the muscles of the right and left ventricle, causing them to depolarize and contract at the same time. Therefore, it can be said that a natural heart contracting impulse travels quickly to all portions of the ventricles, producing a synchronous contraction. This is the natural synchronization of the heart.

AAI leads are known to preserve both atrial ventricular synchronization and the normal ventricular activation and contraction patterns. However, AAI pacing is ineffective in correcting for a damaged AV node or a damaged right/left bundle branch block such as in second or third degree heart block. Presently only ventricular pacing has proved capable of resolving acute problems such as atrioventricular (AV) block or right/left bundle branch block. In ventricular pacing, a voltage pulse typically of 1 Volt/centimeter field strength is used to contract the muscle of the heart. However, ventricular pacing operates somewhat counter to the heart's natural operation. When an electrode located in the apex of the right ventricle delivers the electrical pulse, the myocyte cells local to the apex begin to contract. The electrical signal then expands relatively slowly, compared to the heart's natural contraction, upward and outward until the ventricles fully contract. Therefore, in ventricular pacing the electrical signal travels vertically and laterally from the bottom to the top of the ventricles. This is quite obviously not the heart's natural contraction pattern. Some studies have shown that ventricular pacing not only remodels the heart but this remodeling is associated with congestive heart failure.

Further, some studies have put forth the proposition that significant problems are associated with ventricle pacing. These studies have alleged that, while DDD pacing still preserves atrial ventricular synchronization, it will disrupt ventricular activation and contraction patterns. Moreover, these studies have also alleged that VVI pacing disrupts both atrial ventricular synchronization and ventricular activation and contraction. These studies propose that there is excess mortality in patients receiving ventricular stimulation when compared to stimulation in the upper atrial wall. It has been speculated that this excess mortality is due to heart damage caused by pacing the ventricular apex.

In addition to the problems mentioned above, it has been speculated that ventricular pacing can cause ventricular wall abnormalities due to asynchronous activation and can alter the ventricle volumes. It is speculated that VVI pacing causes heart failure and decreases left ventricular function when compared with AAI pacing. Further, some speculate that DDD chronic ventricular pacing causes a reduced inferior, septum, and global mean myocardial blood flow as well as a decreased left ventricular ejection fraction. These problems are suspected as being due to a reduction in the regional myocardial blood flow. Moreover, several studies have speculated that pacing the right ventricular apex causes these inferior localized myocardial perfusion defects and mitral regurgitation.

Another significant problem is that both DDD and VVI pacing have been alleged to create myofibrilar disarray and fatty deposits throughout the ventricles. Myofibrilar disarray and fatty deposits have been associated with congestive heart failure.

Therefore, what is clearly needed is a method and apparatus for providing atrial ventricular synchronization and proper ventricular activation and contraction for heart patients having AV nodal block, right or left bundle branch block, and in certain circumstances where the heart's intrinsic conduction system is in tact, heart failure. In addition, what is clearly needed is a method and apparatus to prevent remolding of the heart. Further, what is clearly needed is a method and apparatus to prevent inferior myocardial perfusion defects and mitral regurgitation.

SUMMARY OF THE INVENTION

The present invention provides for a medical electrical lead providing pacing to improve the hemodynamics of the heart for patients with AV nodal block, right or left bundle branch block, and in certain circumstances where the heart's intrinsic conduction system is intact, heart failure. The electrical lead is comprised of a lead body having at least one conductor with an electrically insulative sleeve positioned over the conductor. An electrode is disposed at the distal end of the lead body and is electrically connected to the conductor. The electrode is partially masked with an insulative material, leaving an intermediate area unmasked and electrically conductive. The electrode has a helical shape so that it can be screwed into the atrial aspect of the membranous septum or the interventricular septum at a depth substantially near the intrinsic conduction system of the heart either at the common bundle of His or the left or right bundle branches to provide electrical stimulation.

Another aspect of the present invention provides for a method of providing pacing to improve the hemodynamics of the heart for patients with AV nodal block, right or left bundle branch block, and in certain circumstances where the heart's intrinsic conduction system is intact, heart failure. The method comprises the steps of introducing a lead body having at least one conductor with an insulative sleeve into the right atrium of a heart, securing a partially masked helical electrode connected to the conductor into the atrial aspect of the membranous septum or the interventricular septum substantially near the heart's intrinsic conduction system. The electrical conductor is rotated to a particular depth where an unmasked portion of the electrode provides low power pacing of the intrinsic conduction system.

DETAILED DESCRIPTION

Figure 1:
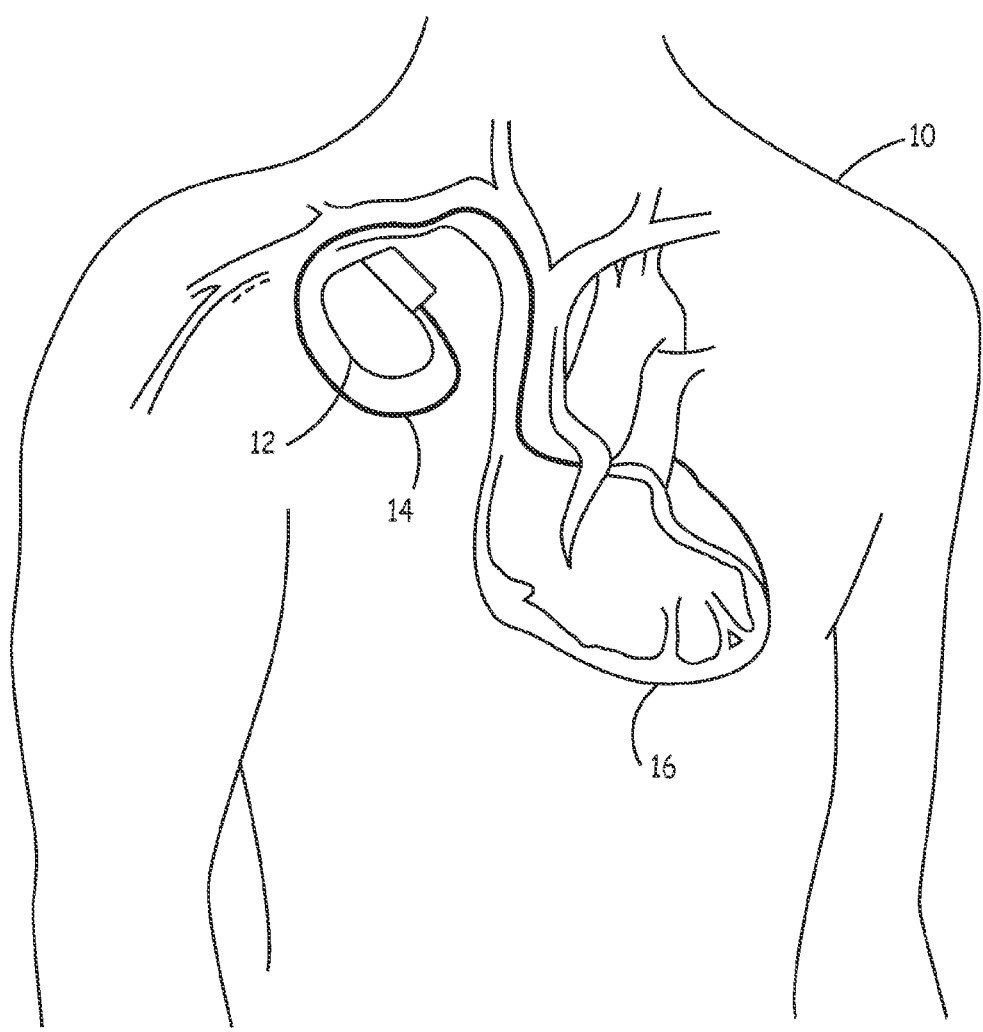
FIG. 1 is a depiction of the venous positioning and placement of a transvenous endocardial lead in a patient.

To assist in an understanding of the invention, a preferred embodiment or embodiments will now be described in detail. Reference will be frequently taken to the figures, which are summarized above. Reference numerals will be used to indicate certain parts and locations in the figures. The same reference numerals will be used to indicate the same parts or locations throughout the figures unless otherwise indicated.

The present invention is not limited to only atrial pacing leads, and may be employed in many of various types of therapeutic or diagnostic devices including nerve, muscle, or defibrillation leads. It is to be further understood, moreover, the present invention may be employed in many of various types of therapeutic or diagnostic catheters and is not limited only to the fixing of electrical leads. For purposes of illustration only, however, the present invention is below described in the context of endocardial pacing leads.

FIG. 1 depicts a typical arrangement of a pacing system implanted in a patient 10, the pacing system comprising a subcutaneously disposed pacemaker 12 and transvenous endocardial pacing lead 14. In FIG. 1, the distal end of pacing lead 14 is shown disposed generally in the atrial region of patient's heart 16, which is discussed below in more detail. However, as discussed above, the lead can also be placed in the interventricular septum.

Figure 2:
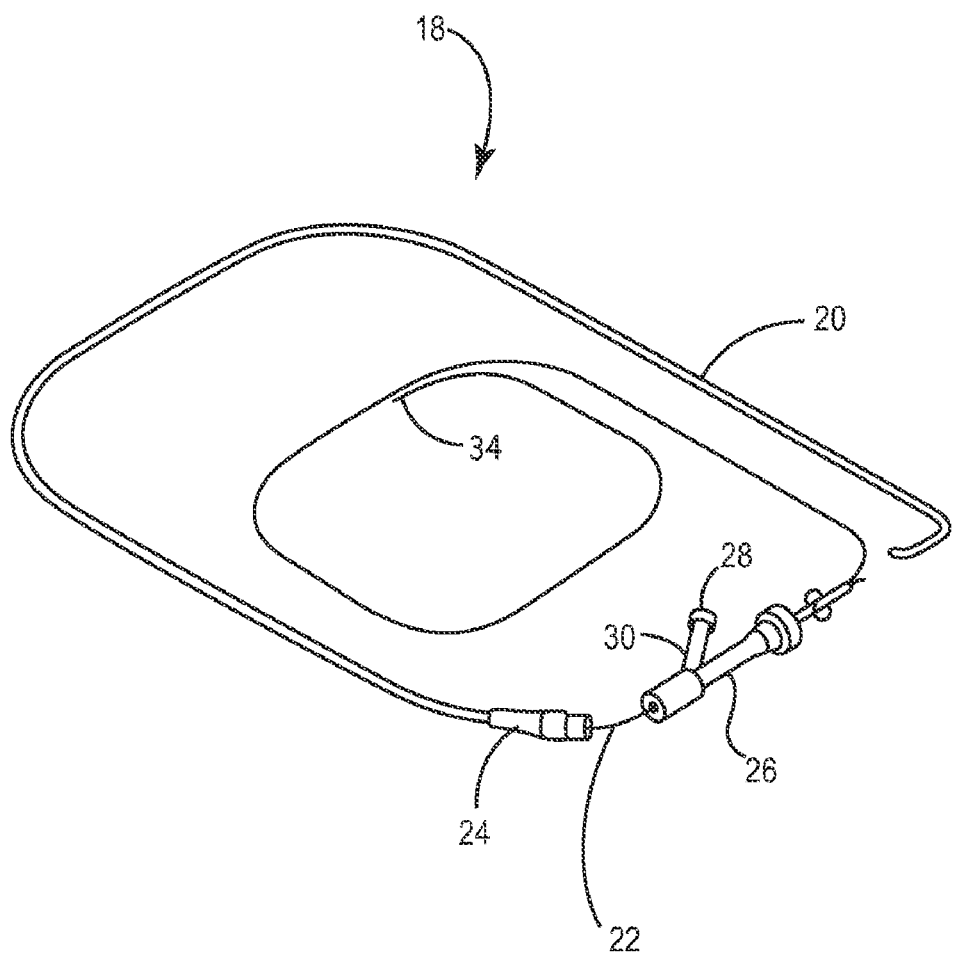
FIG. 2 shows a right perspective view of a preferred embodiment of the pacing lead assembly for the present invention.

FIG. 2 is a right perspective view of a preferred embodiment of a lead assembly utilizing catheter insertion as is well known in the art. As shown lead assembly 18 comprises guide catheter 20 and lead body 22. Lead body 22 is received by and fits slidingly within guide catheter 20. Hub 24 is located at the proximal end of guide catheter 20. Hemostasis valve 26 may be attached to the proximal end of hub 24. Removal of sealing cap 28 from neck 30 permits the introduction of saline solution, anticoagulants, and intravenously administered drugs through valve 26. The proximal end of valve 26 receives lead body 22 and guides it through hub 24 into guide catheter 20.

Figure 3:
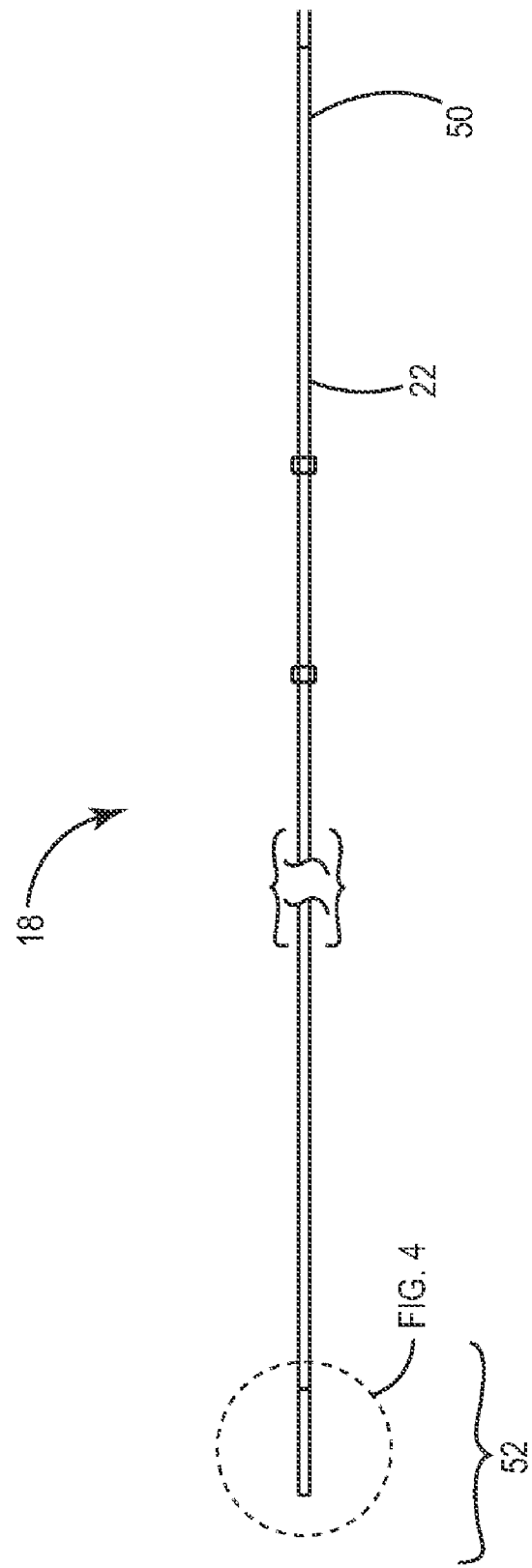
FIG. 3 shows a side view of a preferred embodiment of the lead body of the present invention.
Figure 4:
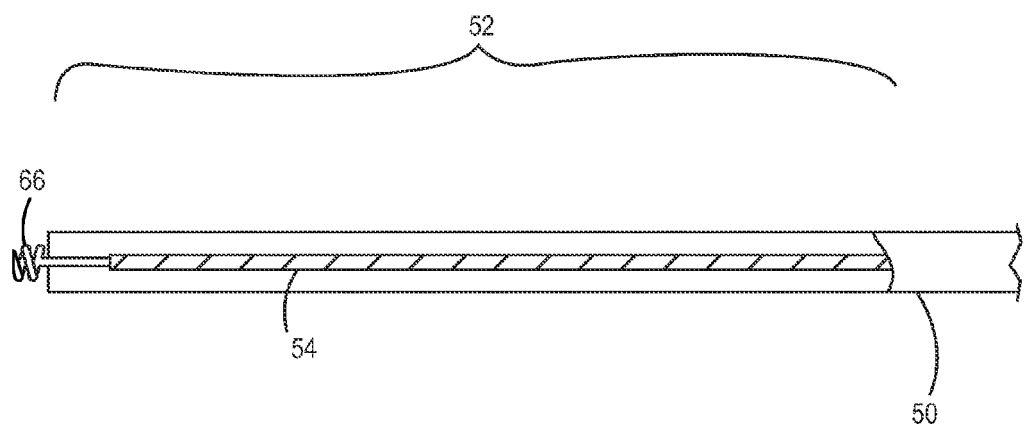
FIG. 4 shows an enlarged axial cross-sectional view of a preferred embodiment of the central portion of the lead body.

With reference to FIGS. 3 and 4, they are a side view of the lead body of a preferred embodiment of a unipolar lead body for the present invention. Lead body proximal end 36 (see FIG. 2) has one conductor 54 for establishing electrical connection between lead assembly 18, a pacemaker, and the tissue of the heart. Preferably, electrically insulative outer sheath 50 is formed of biocompatible material such as a suitable polyurethane or silastic compound, and protects electrical conductor 54 disposed within lead body 22 from the corrosive effects presented by body fluids. Sheath 50 additionally prevents conductor 54 disposed within lead body 22 from shorting to the body. The configuration is preferably introduced with a catheter.

FIG. 4 is an enlarged axial cross-sectional view of lead body distal end 52. Most preferably, conductor 54 comprises three strands of left-hand-wound twisted MP35-N wire, and is capable of reliably conducting electrical current after having been subjected to numerous, repeated bending and torquing stresses. Less preferably, conductor 54 may comprise a single wire formed of a nickel-titanium alloy such as nitinol. Lead body 22 most preferably has a diameter of about 3 French, but may have a diameter as great as about 4 French or as small as about 2 French. Conductor 54 is mechanically and electrically connected to helical screw-in electrode 66. Preferably conductor 54 and electrode 66 are connected by laser welding however other methods of connection are contemplated.

Figure 5:
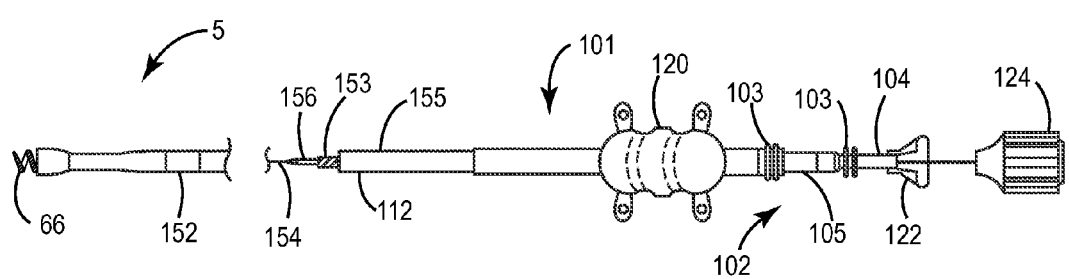
FIG. 5 is a schematic of a body-implantable, endocardial fixed screw lead according to the present invention.

FIG. 5 depicts an alternative embodiment for the configuration of a lead assembly. As seen lead 101 has connector assembly 102 at a proximal end for coupling lead 101 to an implantable pulse generator (not shown). Connector assembly 102 preferably has sealing rings 103, terminal pin 104, and terminal ring 105 all of a type known in the art. Of course, other types of connector assemblies may be used, such as simple pins or even stripped or exposed wire.

An anchoring sleeve 120 may also be provided for suturing lead 101 to body tissue. Anchoring sleeve 120 and connector assembly 102 are preferably fabricated from silicone rubber, although they may also be constructed of any other suitable biocompatible material known in the art, such as polyurethane.

Lead 101 may also include stylet guide 122 and stylet assembly 124 coupled to connector assembly 102 for imparting stiffness to lead 101 during placement. In some designs the stylet may be used for actuation of the lead's fixation mechanism/electrode 66, described below. Stylet guide 122 and stylet assembly 124 are typically discarded after use and before connection of terminal pin 104 to a pulse generator.

Electrode/fixation assembly 66 is disposed at the distal end of lead 101. Lead 101, as shown in FIG. 5, is bipolar, consisting of electrode/fixation assembly 66 and ring electrode 152. Lead 22, as shown in FIG. 2, is unipolar, only having one electrode. As will be appreciated by those of ordinary skill in the art, electrode 66 and ring electrode 152 are coupled to separate, insulated lead conductors that extend along the length of lead body 112. Of course, other electrode configurations may also be used with the present invention, including bipolar or even multipolar designs Electrode 66 used in the lead shown in FIG. 5 is preferably fashioned using a porous platinum composition. The porosity is intended to reduce the foreign body response, stimulation thresholds and signal source impedance and polarization. Although platinum is preferred other materials may also be used, including but not limited to such materials as palladium, titanium, tantalum, rhodium, iridium, carbon, vitreous carbon and alloys, oxides and nitrides of such metals or other conductive or even semi-conductive materials. Of course, some materials are incompatible with others and may not be effectively used together. The limitations of specific materials for use with others are well known in the art. Examples of acceptable electrode materials and associated fabrication techniques employed to achieve the microporous structure may be found in Stokes, U.S. Pat. No. 4,506,680 and related Medtronic U.S. Pat. Nos. 4,577,642; 4,606,118 and 4,711,251 and in the Richter et al., U.S. Pat. No. 4,773,433; Heil Jr. et al., U.S. Pat. No. 4,819,661; Thoren et al., U.S. Pat. No. 4,149,542; Robblee, U.S. Pat. No. 4,677,989; Heil Jr. et al., U.S. Pat. No. 4,819,662; Mund et al., U.S. Pat. No. 4,603,704; Skalsky et al., U.S. Pat. No. 4,784,161; Szilagyi, U.S. Pat. No. 4,784,160, each of which is herein incorporated by reference.

Although not shown in FIG. 5, lead 101 preferably includes a monolithic controlled release device (MCRD) preferably constructed from silicone rubber to elute an anti-inflammatory agent proximate electrode 66. The anti-inflammatory agent, preferably a derivative of dexamethasone, such as the steroid dexamethasone sodium phosphate, is loaded in the MCRD. The steroid also is deposited within electrode 66 material by application of a solution of dexamethasone sodium phosphate dissolved in a mixture of isopropanol and distilled or deionized water. Such agents may or may not be soluble in water (in which case the agent is applied as a coating of the electrode surface), and may include the anti-inflammatory agent beclomethasone, dexamethasone acetate or dexamethasone sodium phosphate.

Lead body 112 has concentric multi-filar conductor coils 153, 154 of a suitable alloy, such as MP35N located between concentric insulative sheaths 155, 156 made of silicone rubber, polyurethane, or the like. This configuration allows for coils 153, 154 to be insulated throughout their respective lengths. Coil 154 is electrically coupled with electrode 66 while coil 153 is electrically coupled with ring electrode 152. A lumen exists along the length of lead body 112, such that a stylet may be received therein. FIG. 5 shows a general configuration of a lead used for the present invention; however, it is contemplated that any lead style or polarization (unipolar, bipolar, or multipolar) could be utilized in the present invention.

Figure 6:
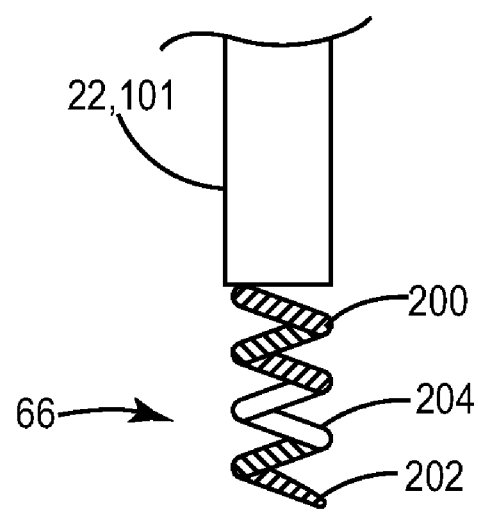
FIG. 6 is a schematic of a partially masked helical electrode according to the present invention.
Figure 8A:
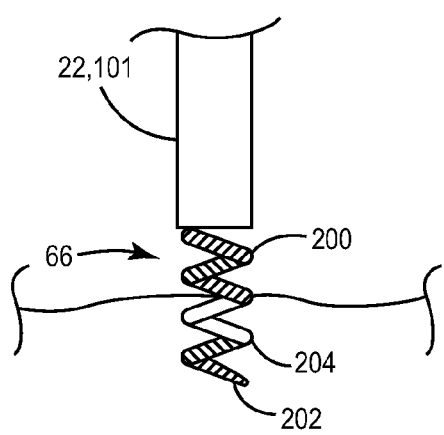
FIG. 8a is a schematic of a partially masked helical electrode partially engaged in heart tissue according to the present invention.
Figure 8B:
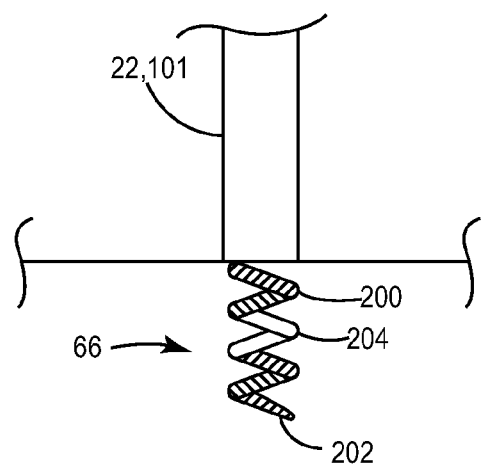
FIG. 8b is a schematic of a partially masked helical electrode fully engaged in heart tissue according to the present invention.

Turning now to FIG. 6, a detailed view of the electrode is shown. As seen, electrode 66 has a masked proximal section 200 and a masked distal section 202. The distal and proximal sections 200 & 202 of helical electrode 66 are masked with an electrically insulative material such as paraline or polyurethane to prevent electrical conduction at the surface of electrode 66 at sections 200 & 202. Electrode 66 also has an intermediate electrically conductive region 204 to allow for pacing at specific depths within the heart tissue. Electrode 66 preferably has a length that allows for pacing of the common bundle of His, which is located at a relatively shallow depth in the tissue of the right atrium. It's length also allows for pacing of the right and left His bundle branches, which are located further away from the AV node in the right atrium, when electrode 66 is in full engagement (FIG. 8b). Further, the right and left His bundle branches could also be paced by placing electrode 66 in high interventricular septum at a shallow depth or partial engagement (FIG. 8a).

In a preferred embodiment, helical coil 66 has an outer diameter of approximately 0.040 inches and an overall length of between 3–6 millimeters. However, varying lengths and diameters are contemplated. Further, helical coil 66 preferably takes at least 2 turns at a millimeter pitch to achieve a stable lead fixation, where a turn is defined as a 360° rotation. In a preferred embodiment, distal end 200 is masked with an insulative material for at least one full turn and unmasked section 204 is unmasked for at least one full turn. Therefore, with at least 1 full turn distal end 200 is implanted to provide fixation and with another full turn unmasked portion 204 is also implanted to not only ensure a stable fixation, but also to prevent any current leakage due to unmasked portion 204 being exposed to blood in the heart. As stated above, unmasked portion 204 is unmasked for 1 full turn. This is to ensure proper electrical stimulation. For example, if section 204 was only unmasked on a quarter of a turn it may be difficult to place the unmasked portion close enough to the target area during overshot during implantation. It is of note, that exposed region 204 is proximal to the distal end of electrode 66 to allow for less than full helix engagement and still maintain a stable lead fixation. This means that when exposed region 204 is fully within the heart's tissue there is enough turns of helical electrode 66 in the heart's tissue to provide stable lead fixation, which is discussed below in more detail.

Figure 7A:
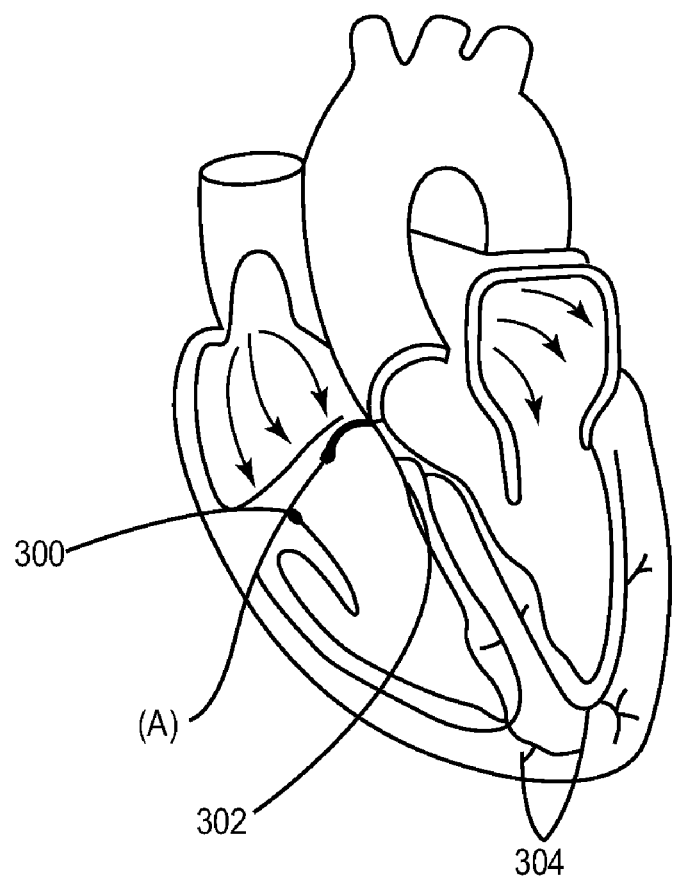
FIG. 7a is a depiction of the intrinsic conduction system of the heart.

In contrast to ventricular pacing, activating the His bundle by stimulation low in the atrial septum 300 or high in the interventricular septum 302 has been found to be similar to natural stimulation, since depolarization then comes via the Purkinje 304 system and subsequently spreads rapidly across the ventricle with more efficient heartbeats as a result. Therefore, with reference to FIG. 7a, the present invention provides pacing utilizing the heart's intrinsic conduction system to improve the atrial ventricular synchronization, ventricular activation, and ventricular contraction. Upon a patient being diagnosed with a particular ailment in the heart's intrinsic conduction system, the physician would determine which portion of the heart's intrinsic conduction system is not working properly. For example, if it was determined that the AV node, shown approximately at (A) in FIG. 7a, was not functioning properly, or at all, then the physician could pace the ventricles using the heart's intrinsic conduction system (e.g., the His bundle) if the rest of the intrinsic conduction system is working properly.

Figure 7B:
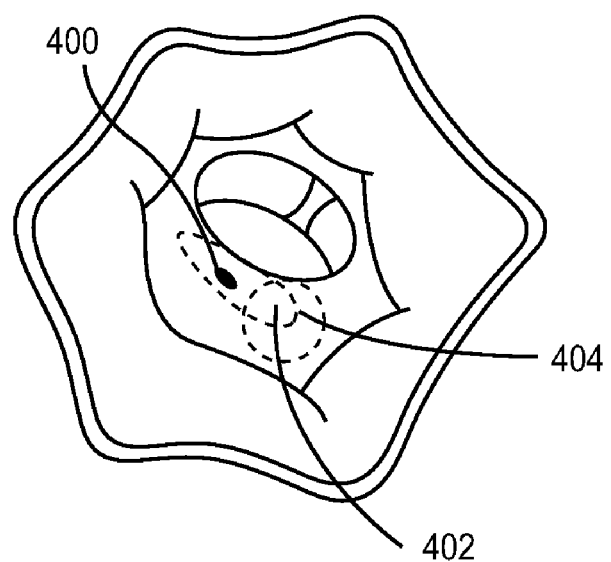
FIG. 7b is a depiction of a portion of the intrinsic conduction system of the heart near the AV node.

Continuing with the example above and with reference to FIG. 7b, the physician begins by implanting lead 18, 101 into the right atrium, for His bundle pacing, and in the upper right ventricle for right or left bundle branch pacing. The physician then looks for landmarks close to the AV node 400. Using a fluoroscope, the physician looks for the boundaries of the triangle of Koch 402, which contain the His bundle 404 at its apex. Upon finding this landmark the physician would implant electrode 66 in a location believed to be located down the electrical path of an improperly working portion of the intrinsic conduction system. In the example above, this location is the His bundle. The physician then begins to stimulate the intrinsic conduction system. During the stimulation the physician will rotate electrode 66 in and out of the tissue to determine an optimal position in which to pace the portion of the intrinsic conductive system. The intrinsic conductive system lies within the hearts tissue. Since the depth at which the intrinsic system lies is different for every person, the physician rotates helical electrode in and out of the tissue to determine an optimal conductive position. Typically, the optimal conductive position is when conductive region 204 is rotated substantially close or adjacent to the intrinsic conductive system point where pacing is desired. By having electrode 66 in an optimal conductive position less current is used in the pacing of the intrinsic conductive system and thus the pacemaker's battery will last longer. This helps reduce the number of subsequent surgeries the pacemaker patient needs to incur. This is preferable to pacing the right ventricular myocardium.

With reference to FIG. 8a & 8b, a partial and full engagement of helical electrode 66 is shown. As can be seen distal masked section 202 and exposed region 204 are fully within the heart tissue and proximal masked section 200 is either partially or fully within the heart tissue. The partial engagement connection shown in FIG. 8a can be used in situations where the best conductive path to the desired intrinsic conduction system of the heart has a shallow location within the heart tissue. As stated above, the intrinsic conduction system of heart 16 can be located at different depths within the heart tissue. The full engagement connection shown in FIG. 8b can be used in situations where the best conductive path to the desired intrinsic conduction system of the heart has a deep location within the heart tissue, such as pacing the His bundle or the right or left branch bundle.

Since blood is very conductive, it is preferred that proximal masked section 200 be fully or partially engaged in the heart tissue to prevent current leakage from the conductivity of the blood. By having proximal masked section 200 partially or fully engaged in the heart tissue it is ensured that no portion of exposed section 204 is exposed to blood in the atrial chamber and thus current leakage is kept to a minimum. If the distal end of helical electrode 202 was unmasked and the rest of electrode 66 was either unmasked or masked, then it would be difficult to use lead 18, 101 in applications where the optimal conductive position was located at a shallow distance within the heart's tissue such as is the case for the right bundle branch. If optimal conductive path is located in a shallow position and the rest of the electrode was masked then the helical electrode could not be screwed into the heart tissue adequately enough to give a secure placement of lead 18, 101. If electrode 66 was not masked at all and then fully engaged in order to stimulate the shallow position of the best conductive path without having current leakage, then current could be wasted throughout the entire length of electrode 66 because the entire length of electrode 66 is electrically conductive and touching electrically conductive tissue. If electrode 66 was only screwed half way in to provided a secure connection and to stimulate the shallow position of the best conductive path, then not only would there be excess current wasted by the transfer of current into the heart tissue, but there would also be excess current wasted due to the exposed electrode 66 making contact with highly conductive blood.

By having partially masked electrodes a more precise field can be produced to stimulate either the His bundle, high interventricular septum, or the right/left ventricle. By pacing the intrinsic conduction system of the heart or the high septum a more rapid and uniform depolarization of the ventricles will occur. This in effect better synchronizes the ventricular contractions.

While the invention has been described in the context of the fixing of endocardial pacing leads, the present invention is not limited to only endocardial leads, but may also be used within a myocardial or epicardial lead. Indeed, the present invention is not limited to only fixed cardiac pacing leads, and may be employed in fixing many of various types of therapeutic or diagnostic devices including nerve, muscle or sensing with defibrillation leads. It is to be further understood, moreover, the present invention may be employed in many of various types of therapeutic or diagnostic catheters and is not limited only to the fixing of only electrical leads.

Finally, although the invention has been described in detail with particular reference to a preferred embodiment and alternate embodiments thereof, it will be understood variations and modifications can be effected within the scope of the following claims. Such modifications may include substituting elements or components, which perform substantially the same function in substantially the same way to achieve substantially the same result for those described herein.

Thus, embodiments of the Physiologic Pacing Method and apparatus for Heart Block is disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A pacing system comprising:
   a medical lead including:
      a lead body having at least one conductor with an electrically insulative sleeve positioned over the conductor;
      an electrode disposed at a distal end of the lead body, the electrode co-linear to the lead body, said electrode electrically connected to the conductor, said electrode having a shape adapted to provide fixation into tissue of a heart;
      an electrically insulative material masking proximal and distal ends of the electrode; and
      an intermediate unmasked conductive portion of the electrode positioned between the masked proximal and distal ends of the electrode, wherein the medical lead adapted to couple to one of a HIS bundle and a right ventricular septum of a heart,
   wherein the distal end of the electrode being masked along a sufficient length of the electrode such that insertion of only the masked distal end and the unmasked portion in the heart tissue provides stable fixation.

2. The pacing system of claim 1, wherein at least one full turn of the electrode of the unmasked portion being unmasked.

3. The pacing system of claim 2, wherein at least one full turn of the electrode masked along the distal end.

4. The pacing system of claim 3, wherein at least one full turn of the electrode being masked at the proximal end.

5. The pacing system of claim 1, wherein the lead body being comprised of an insulative material.

6. The pacing system of claim 1, wherein the conductor being a helical coil.

7. The pacing system of claim 1, wherein the conductor being an elongated conductor.

8. The pacing system of claim 1, wherein the lead body being a bipolar lead body.

9. The pacing system of claim 1, wherein the lead body being a multipolar lead body.

10. The pacing system of claim 1, wherein the unmasked portion of the electrode being centered on the electrode.

11. The pacing system of claim 1, wherein the insulative material being a substantially inert material.

12. The pacing system of claim 1, wherein the helical electrode has a length of not less than 3 millimeters.

13. The pacing system of claim 12, wherein the helical electrode provides stable fixation after three turns of the electrode.

14. A method for stimulating a heart comprising the steps of:
   introducing a lead body having at least one conductor with an insulative sleeve into the right side of a heart;
   connecting a partially masked helical electrode with the at least one conductor, the electrode co-linear to the lead body with an electrically insulative material masking proximal and distal ends of the electrode;
   securing the partially masked helical electrode, adapted to couple, to one of a HIS bundle and a right bundle branch of a heart; and
   rotating the electrical conductor such that an unmasked portion of the electrode being at a depth substantially near the heart's intrinsic conduction system to provide low power paced stimulation of the intrinsic conduction system;
   wherein the distal end of the electrode being masked along a sufficient length of the electrode such that rotation of only the masked distal end and the unmasked portion into the heart tissue provides stable fixation.

15. The method of claim 14, wherein the lead body being comprised of an insulative material.

16. The method of claim 14, wherein the conductor being a helical coil.

17. The method of claim 14, wherein the conductor being an elongated conductor.

18. The method of claim 14, wherein the lead body being a bipolar lead body.

19. The method of claim 14, wherein the lead being a multipolar lead body.

20. The method of claim 14, wherein the unmasked portion of the electrode being centered on the electrode.

21. The method of claim 14, wherein the insulative material being a substantially inert material.

22. The method of claim 14, wherein the electrode being at least 3 millimeters long.

* * * * *